(12) United States Patent
Itagaki et al.

(10) Patent No.: US 10,919,836 B2
(45) Date of Patent: *Feb. 16, 2021

(54) PRODUCTION METHOD OF ALIPHATIC CARBOXYLIC ACID ESTER

(71) Applicant: SHOWA DENKO K.K., Tokyo (JP)

(72) Inventors: Shintaro Itagaki, Oita (JP); Katsuhiko Yamashita, Oita (JP); Taku Takahashi, Oita (JP)

(73) Assignee: SHOWA DENKO K.K., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/639,932

(22) PCT Filed: Sep. 3, 2018

(86) PCT No.: PCT/JP2018/032659
§ 371 (c)(1),
(2) Date: Feb. 18, 2020

(87) PCT Pub. No.: WO2019/049838
PCT Pub. Date: Mar. 14, 2019

(65) Prior Publication Data
US 2020/0239399 A1    Jul. 30, 2020

(30) Foreign Application Priority Data
Sep. 5, 2017 (JP) .............................. JP2017-170158

(51) Int. Cl.
| C07C 67/04 | (2006.01) |
| B01J 21/08 | (2006.01) |
| B01J 35/00 | (2006.01) |
| B01J 35/02 | (2006.01) |
| B01J 35/10 | (2006.01) |
| B01J 37/00 | (2006.01) |
| B01J 37/02 | (2006.01) |

(52) U.S. Cl.
CPC .............. *C07C 67/04* (2013.01); *B01J 21/08* (2013.01); *B01J 35/0026* (2013.01); *B01J 35/023* (2013.01); *B01J 35/1019* (2013.01); *B01J 35/1038* (2013.01); *B01J 37/0018* (2013.01); *B01J 37/0211* (2013.01)

(58) Field of Classification Search
CPC ...... B01J 21/08; B01J 35/0026; B01J 35/023; B01J 35/1019; B01J 35/1038; B01J 37/0018; B01J 37/0211; B01J 27/188; B01J 35/08; B01J 35/1061; B01J 35/1066; B01J 35/1071; B01J 37/0201; B01J 35/00; C07C 67/04; C07C 69/14
See application file for complete search history.

(56) References Cited

U.S. PATENT DOCUMENTS

| 6,187,949 B1 * | 2/2001 | Froom ................... C07C 67/04 560/247 |
| 6,624,325 B1 | 9/2003 | Higashi et al. |
| 2005/0063890 A1 | 3/2005 | Nakanishi |
| 2008/0255390 A1 * | 10/2008 | Bosch ...................... B01J 21/12 564/469 |
| 2010/0331571 A1 * | 12/2010 | Saito ..................... C04B 35/478 562/532 |
| 2013/0165608 A1 | 6/2013 | Siegel et al. |
| 2013/0289145 A1 * | 10/2013 | Miura .................. B01J 37/0009 518/715 |

FOREIGN PATENT DOCUMENTS

| CA | 1087595 A | 10/1980 |
| EP | 0 757 027 A1 | 2/1997 |
| GB | 2 385 287 A | 8/2003 |
| GB | 2385287 * | 8/2003 |
| GB | 2 398 749 A | 9/2004 |
| JP | 54-160490 A | 12/1979 |
| JP | 62-252378 A | 11/1987 |
| JP | 9-118647 A | 5/1997 |
| JP | 2000-342980 A | 12/2000 |
| JP | 2004-148177 A | 5/2004 |
| JP | 2008-513534 A | 5/2008 |
| JP | 2015-221746 A | 12/2015 |
| JP | 2016-199444 A | 12/2016 |
| WO | 00/03967 A1 | 1/2000 |
| WO | 00/45952 A1 | 8/2000 |
| WO | 2006/032843 A1 | 3/2006 |

OTHER PUBLICATIONS

Brame et al. (Surface area Analysis Using the Brunauer-Emmett-Teller (BET) Method, p. 1-4, Published Sep. 2016) (Year: 2016).*
Hiden (Glossary: Barrett-Joyner-Halenda (BJH) Analysis, p. 1-2, Published Dec. 2013) (Year: 2013).*
International Search Report of PCT/JP2018/032659 dated Jan. 21, 2019 [PCT/ISA/210].
Written Opinion of PCT/JP2018/032659 dated Jan. 21, 2019 [PCT/ISA/237].
International Search Report of related PCT/JP2018/032664 dated Nov. 27, 2018 [PCT/ISA/210].
Written Opinion of related PCT/JP2018/032664 dated Nov. 27, 2018 [PCT/ISA/237].

* cited by examiner

*Primary Examiner* — Yevgeny Valenrod
*Assistant Examiner* — Blaine G Doletski
(74) *Attorney, Agent, or Firm* — Sughrue Mion, PLLC

(57) ABSTRACT

In a method for producing an aliphatic carboxylic acid ester by reacting an aliphatic carboxylic acid having from 1 to 5 carbon atoms and an olefin having from 2 to 4 carbon atoms in a gas phase by use of a solid acid catalyst, a solid acid catalyst in which a heteropolyacid or a salt thereof is supported on a silica carrier obtainable by kneading fumed silica obtained by a combustion method, silica gel obtained by a gel method, and colloidal silica obtained by a sol-gel method or a water glass method, molding the resulting kneaded product, and calcining the resulting molded body, is used.

9 Claims, 2 Drawing Sheets

PRODUCTION METHOD OF ALIPHATIC CARBOXYLIC ACID ESTER

CROSS REFERENCE TO RELATED APPLICATIONS

This application is a National Stage of International Application No. PCT/JP2018/032659, filed Sep. 3, 2018, claiming priority to Japanese Patent Application No. 2017-170158, filed Sep. 5, 2017.

FIELD

The present invention relates to a method for producing an aliphatic carboxylic acid ester by reacting an aliphatic carboxylic acid having from 1 to 5 carbon atoms and an olefin having from 2 to 4 carbon atoms in a gas phase by use of a solid acid catalyst.

BACKGROUND

It is well known that a corresponding ester can be produced by a gas phase catalytic reaction of a lower aliphatic carboxylic acid and lower olefins. Furthermore, it is also well known that a catalyst composed of a heteropolyacid and/or a salt thereof supported on a siliceous carrier is useful for the above reaction (Patent Documents 1 to 4).

For example, Patent Document 1 describes producing a lower aliphatic carboxylic acid ester by bringing a lower aliphatic carboxylic acid and a lower olefin into contact with a heteropolyacid catalyst supported on a silica carrier in a gas phase. In Patent Document 1, as the heteropolyacid suitable as an active species, silicotungstic acid, phosphotungstic acid, etc., and salts thereof are described. In addition, as a suitable carrier, a silica carrier prepared by pelletizing fumed silica is described.

It is widely known that a silica carrier is used as the catalyst carrier in the petrochemical and petroleum refining fields. It is also known that properties of the silica carrier used in the catalyst, such as surface area, pore volume, bulk density, hydrophilicity, hydrophobicity and strength, greatly affect the performance of the catalyst. As to the catalyst used for the production of a lower aliphatic carboxylic acid ester, improvements of silica carrier have also been made thus far with the purpose to enhance the performance.

In Patent Document 2, a silica carrier in which the value of specific surface area by the BET method is in a specific range of values is disclosed as a carrier suitable to enhance the catalytic activity of the catalyst used for producing a lower aliphatic carboxylic acid ester.

In Patent Document 3, a silica carrier in which the alkali metal content in the carrier is reduced to a specific value by carrying out acid cleaning is disclosed as a carrier suitable to enhance the catalytic activity of the catalyst used for producing a lower aliphatic carboxylic acid ester.

In Patent Document 4, a silica carrier subjected to a steam treatment under specific conditions is disclosed as a carrier suitable for the catalyst to reduce the amount of reaction byproducts in the production of a lower aliphatic carboxylic acid ester.

CITATION LIST

Patent Literature

[PTL 1] Japanese Unexamined Patent Publication (Kokai) No. 09-118647

[PTL 2] Japanese Unexamined Patent Publication (Kokai) No. 2000-342980

[PTL 3] International Publication No. 2000/045952

[PTL 4] National Publication of Translated Version (Kohyo) No. 2008-513534

SUMMARY

Technical Problem

In all of Patent Documents 1 to 4, as a result of various efforts in regard to the properties of a silica carrier, the target lower aliphatic ester can be obtained with a relatively high space-time yield. However, a high-performance catalyst exhibiting a higher space-time yield than these conventional techniques is demanded at present.

An object of the present invention is to increase the activity of a solid acid catalyst used for the production of an aliphatic carboxylic acid ester and thereby achieve efficiency enhancement in the production of an aliphatic carboxylic acid ester.

Solution to Problem

As a result of studies, the present inventors have found that a silica carrier obtainable by kneading fumed silica obtained by a combustion method, silica gel obtained by a gel method, and colloidal silica obtained by a sol-gel method or a water glass method (ion exchange method), molding the resulting kneaded product, and calcining the resulting molded body is excellent as a carrier because of having a large pore volume of macropores and a large BET specific surface area at the same time and when a heteropolyacid is supported thereon, exhibits high activity in a reaction for producing a corresponding ester by a gas phase catalytic reaction of a lower aliphatic carboxylic acid and lower olefins. The present invention has been accomplished based on this finding.

That is, the present invention relates to the following [1] to [10].

[1] A method for producing an aliphatic carboxylic acid ester by reacting an aliphatic carboxylic acid having from 1 to 5 carbon atoms and an olefin having from 2 to 4 carbon atoms in a gas phase by use of a solid acid catalyst, the method including using a solid acid catalyst in which a heteropolyacid or a salt thereof is supported on a silica carrier obtainable by kneading fumed silica obtained by a combustion method, silica gel obtained by a gel method, and colloidal silica obtained by a sol-gel method or a water glass method, molding the resulting kneaded product, and calcining the resulting molded body.

[2] The method for producing an aliphatic carboxylic acid ester according to [1], wherein the blending amount of fumed silica is from 5 to 50 parts by mass, the blending amount of silica gel is from 40 to 90 parts by mass, and the blending amount of the solid content of colloidal silica is from 5 to 30 parts by mass.

[3] The method for producing an aliphatic carboxylic acid ester according to [1] or [2], wherein the calcining temperature is from 300 to 1,000° C.

[4] A method for producing an aliphatic carboxylic acid ester by reacting an aliphatic carboxylic acid having from 1 to 5 carbon atoms and an olefin having from 2 to 4 carbon atoms in a gas phase by use of a solid acid catalyst, the method including using a solid acid catalyst in which a heteropolyacid or a salt thereof is supported on a silica carrier having, in the measurement of pore size distribution, mesopores with a pore size of 2 to 50 nm and macropores with a pore size of more than 50 nm and 1,000 nm or less.

[5] The method for producing an aliphatic carboxylic acid ester according to [4], wherein in the pore size distribution by mercury intrusion porosimetry, the pore volume of macropores of the silica carrier is from 0.05 to 0.50 cc/g.

[6] The method for producing an aliphatic carboxylic acid ester according to [4] or [5], wherein the BET specific surface area of the silica carrier is from 200 to 500 $m^2/g$.

[7] The method for producing an aliphatic carboxylic acid ester according to any one of [4] to [6], wherein the bulk density of the silica carrier is from 300 to 700 g/L.

[8] The method for producing an aliphatic carboxylic acid ester according to any one of [4] to [7], wherein the average pore size of mesopores by the BJH method of the silica carrier is from 3 to 16 nm.

[9] The method for producing an aliphatic carboxylic acid ester according to any one of [4] to [8], wherein the particle diameter of the silica carrier is from 2 to 8 mm.

[10] The method for producing an aliphatic carboxylic acid ester according to any one of [4] to [9], wherein the silica carrier is obtainable by kneading fumed silica obtained by a combustion method, silica gel obtained by a gel method, and colloidal silica obtained by a sol-gel method or a water glass method, molding the resulting kneaded product, and calcining the resulting molded body.

Advantageous Effects of Invention

According to the present invention, a highly active solid acid catalyst in which a heteropolyacid or a salt thereof is supported on a silica carrier having a specific structure is used for the production of an aliphatic carboxylic acid ester by the reaction of a carboxylic acid having from 1 to 5 carbon atoms, for example, acetic acid, with an olefin having from 2 to 4 carbon atoms, for example, ethylene, and the production efficiency can thereby be enhanced.

DESCRIPTION OF EMBODIMENTS

Figure 1:
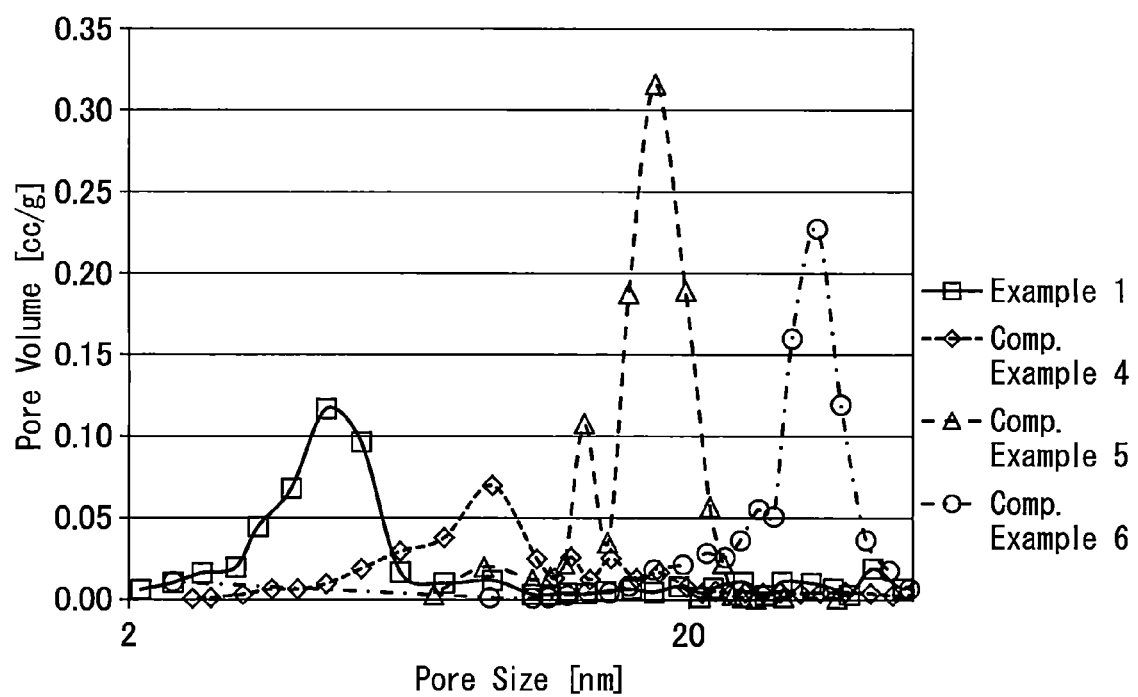
FIG. 1 A graph illustrating the pore size distribution by the BJH method of the silica carriers used in Example 1 and Comparative Examples 4 to 6.

Preferred embodiments of the present invention are described below, however, the present invention is not limited only to these embodiments, and it should be understood that various applications are possible within the spirit and scope of implementation of the present invention.

(Silica Carrier)

In general, synthetic amorphous silica is produced by either a dry process or a wet process. The combustion method of burning silicon tetrachloride in a hydrogen flame in the presence of oxygen is classified into the dry process, and a gel method of allowing the neutralization reaction of sodium silicate and a mineral acid to proceed in an acidic pH region and thereby causing aggregation in the state of growth of primary particles being suppressed, a sol-gel method of carrying out hydrolysis of alkoxysilane, and a water glass method of preparing active silicic acid by ion-exchanging of sodium silicate and growing particles in a seed particle-containing aqueous solution at an adjusted pH under heating, are classified into the wet process. In general, silica obtained by a combustion method is referred to as fumed silica, silica obtained by a gel method is referred to as silica gel, and silica after dispersing silica particles obtained by a sol-gel method or a water glass method in a medium, such as water, is referred to as colloidal silica.

A silica carrier of one embodiment is obtainable by kneading fumed silica obtained by a combustion method, silica gel obtained by a gel method, and colloidal silica obtained by a sol-gel method or a water glass method, molding the resulting kneaded product, and calcining the resulting molded body.

In the case of kneading fumed silica, silica gel and colloidal silica and subjecting the kneaded product to molding process and calcining, for example, the sizes of primary particle and secondary particle of the silica carrier after calcining and the internal state of a porous body are changed by the blending ratio of respective components, the kneading method, the calcining conditions, etc., and therefore, the high-order structure of the silica carrier of the present invention cannot be specified. The composition formula of the silica carrier is $SiO_2$.

There is no limit on the fumed silica, and a general fumed silica can be used. Examples of the commercially available fumed silica may include AEROSIL (trademark) produced by Nippon Aerosil Co., Ltd., REOLOSIL (trademark) produced by Tokuyama Corporation, and CAB-O-SIL (trademark) produced by Cabot Corporation. The commercially available fumed silica includes hydrophilic and hydrophobic grades, and both can be used. A typical fumed silica is characterized by having, as physical property values, for example, a primary particle diameter of 7 to 40 nm and a specific surface area of 50 to 500 $m^2/g$, being not porous but being amorphous with no internal surface area, having a high purity of 99% or greater in terms of silicon oxide, and containing substantially no metal and no heavy metal.

There is no limit also on the silica gel, and a general silica gel can be used. Examples of the commercially available silica gel may include NIPGEL produced by Tosoh Silica Corporation, MIZUKASIL produced by Mizusawa Industrial Chemicals, Ltd., CARiACT produced by Fuji Silysia Chemical Ltd., and SUNSPHERE produced by AGC Si-Tech Co., Ltd. In general, silica gel is produced using, as a raw material, sodium silicate that is obtainable by mixing and melting silica sand ($SiO_2$) and soda ash ($Na_2CO_3$) and dissolving the obtained sodium silicate glass (cullet) in water, by carrying out a reaction of sodium silicate with a mineral acid, such as sulfuric acid, under acidic conditions, and causing aggregation in the state of growth of primary particles being suppressed, thereby gelling the entire reaction solution. The physical properties of the silica gel are not particularly limited, but the silica gel is characterized in that the primary particle is small, the specific surface area is high, and the secondary particle is hard. Examples of specific physical properties of the silica gel include a BET specific surface area of 200 to 1,000 $m^2/g$, a secondary particle diameter of 1 to 30 μm, and a pore volume of 0.3 to 2.5 mL/g as measured by a nitrogen gas adsorption method (BJH method). The higher the purity of silica gel, the better, and the purity is preferably 95 mass % or greater, more preferably 98 mass % or greater.

The colloidal silica is also not particularly limited, and a general colloidal silica can be used. Examples of the commercially available colloidal silica may include SNOWTEX (trademark) produced by Nissan Chemical Corporation, SILICADOL produced by Nippon Chemical Industrial Co., Ltd., ADELITE produced by ADEKA Corporation, CAB-O-SIL (trademark) TG-C Colloidal Silica produced by Cabot Corporation, and QUARTRON produced by Fuso Chemical Co., Ltd. The colloidal silica is obtained by dispersing silica fine particles in a medium, such as water. The production method for colloidal silica includes a water glass method and a sol-gel method by the hydrolysis of alkoxysilane, and a colloidal silica produced by either production method can be used. A colloidal silica produced by a water glass method and a colloidal silica produced by a sol-gel method may be used in combination. Typical physical properties of the colloidal silica include a particle diameter of 4 to 80 nm and a solid content concentration of silica dispersed in water or an organic solvent of 5 to 40 mass %. The impurity concentration in the colloidal silica may affect the catalytic active component supported thereon and is therefore preferably lower. The silica purity in the solid content is preferably 99 mass % or greater, more preferably 99.5 mass % or greater.

The silica carrier can be obtained by kneading fumed silica, silica gel, and colloidal silica, molding the resulting kneaded product, and calcining the molded body. At the time of kneading, an appropriate additive may be added. The blending ratio of fumed silica, silica gel and colloidal silica is preferably set to be from 5 to 50 parts by mass of fumed silica, from 40 to 90 parts by mass is silica gel, and from 5 to 30 parts by mass of the solid content of colloidal silica, more preferably from 15 to 40 parts by mass of fumed silica, from 45 to 70 parts by mass of silica gel, and from 5 to 15 parts by mass of the solid content of colloidal silica.

At the time of mixing of fumed silica, silica gel, and colloidal silica, water or an additive may be added with the purpose of, for example, improving the moldability and enhancing the strength of the final silica carrier. The additive is not particularly limited, and an additive employed when producing a general ceramic molded material may be used. A binder, a plasticizer, a dispersant, a lubricant, a wetting agent, a defoaming agent, etc., may be used depending on the purpose.

The binder may include wax emulsion, gum arabic, lignin, dextrin, polyvinyl alcohol, polyethylene oxide, starch, methyl cellulose, Na-carboxymethyl cellulose, hydroxyethyl cellulose, sodium alginate, ammonium alginate, tragacanth gum, etc. The viscosity of the kneaded product greatly varies depending on the type and concentration of the binder and therefore, the type and amount of the binder are selected to provide a suitable viscosity for the molding method used.

The plasticizer may include glycerin, polyethylene glycol, dibutyl phthalate, etc., and can increase the flexibility of the kneaded product.

The dispersant may include, as an aqueous dispersant, carboxymethyl cellulose ammonium (CMC-NH$_4$), an oligomer of acrylic acid or an ammonium salt thereof, an anionic surfactant, ammonium polycarboxylate, wax emulsion, various amines, such as monoethylamine, pyridine, piperidine, tetramethylammonium hydroxide, etc., and may include, as a nonaqueous dispersant, a fatty acid, a fatty acid ester, a phosphoric acid ester, a synthetic surfactant, benzenesulfonic acid, etc. When such a dispersant is added, a silica carrier having a uniform microstructure after calcining can be obtained by virtue of avoiding production of agglomerated particles.

The lubricant may include a hydrocarbon-based lubricant, such as liquid paraffin, paraffin wax and chlorinated hydrocarbon, a fatty acid-based lubricant, such as stearic acid, lauric acid and a metal salt thereof, a fatty acid amide-based lubricant, etc. When the lubricant is added, molding is facilitated by virtue of reducing friction between powders and improving fluidity and in addition, the molded article is easily removed from the mold.

A wetting agent can be added so as to enhance the wetting property of the powder and dispersant. The wetting agent may include, as an aqueous wetting agent, a nonionic surfactant, alcohol and glycol and may include, as a non-aqueous wetting agent, polyethylene glycol ethyl ether, polyoxyethylene ester, etc. Such a substance is readily adsorbed on the solid-liquid interface and reduces the interfacial tension to thereby improve wetting of a solid.

In the case of handling a slurried kneaded product, a defoaming agent, such as a nonionic surfactant, polyalkylene glycol derivative and polyether derivative, may also be added.

One of these additives may be used alone, or a plurality thereof may be used at the same time in combination, but it is preferable to produce an effect with as a small amount as possible, be inexpensive, be incapable of reacting with the powder, dissolve in water or a solvent, be completely decomposed in an oxidizing or non-oxidizing atmosphere, for example, at a relatively low temperature of 400° C. or less, prevent ash, particularly, an alkali metal and a heavy metal, from remaining after decomposition explosion, generate a non-toxic non-corrosive decomposition gas, and allow for reutilization of a fragment that has not become a product.

The shape of the silica carrier is not particularly limited. The shape may include, for example, a spherical shape, a columnar shape, a hollow columnar shape, a plate-like shape, an elliptical shape, a sheet shape, and a honeycomb shape. The shape is preferably a spherical, columnar, hollow columnar or elliptical shape that facilitates filling a reactor and supporting a catalytic active component, more preferably a spherical or columnar shape.

The method for molding the silica carrier is not particularly limited, and the carrier is molded from a kneaded product containing fumed silica, silica gel and colloidal silica by any convenient method, such as mold-pouring molding, extrusion molding, tumbling granulation and spray drying. A general mold-pouring molding is also referred to as stamp molding, in which the kneaded product is put in a metal-made mold, closely packed while striking by a hammer, etc., pressurized by a piston, and then taken out of from the mold. The extrusion molding generally includes charging the kneaded product in a press, extruding through a die (spinneret), cutting to an appropriated length, and molding into a desired shape. The tumbling granulation includes dropping the kneaded product on an obliquely placed rotary disc, and rolling and growing particles on the disk into a spherical shape. The spray drying includes spraying a thick slurry into hot air to obtain a porous particle, although the particle may not be increased in size.

The size of the silica carrier is not particularly limited. The size affects, for example, the handling during production of a catalyst on which a catalytic active component is supported, or during filling with the catalyst, the differential pressure after the reactor is filled, and the reaction results of catalytic reaction and therefore, is preferably selected in consideration of these. The size of the silica carrier is determined by the calcining conditions, since shrinkage of the carrier occurs during fining of the molded body. As for the size of the silica carrier (after calcining), in the case where the silica carrier is spherical, the diameter is preferably from 0.5 mm to 12 mm, more preferably from 1 mm to 10 mm, more preferably from 2 mm to 8 mm. In the case where the silica carrier has a non-spherical shape, the size of the silica carrier (after calcining) is, as the length of a maximum dimension when the size is measured, preferably from 0.5 mm to 12 mm, more preferably from 1 mm to 10 mm, still more preferably from 2 mm to 8 mm. When the particle diameter of the silica carrier is 0.5 mm or greater, a reduction in the productivity at the time of carrier production and an increase in the pressure loss when used as a catalyst can be prevented. When the particle diameter of the silica carrier is 12 mm or less, a reduction in the reaction rate due to diffusion control and an increase of byproducts can be prevented.

The shape of the silica carrier can also be adjusted by carrying out, if desired, a treatment using Marumerizer (trademark; spheronizer machine) (Fuji Paudal Co., Ltd.), etc., before or after calcining. For example, the columnar molded body before calcining can be formed to be spherical by a treatment with the Marumerizer.

The calcining method is not particularly limited, but from the viewpoint of decomposing the additive and preventing structural disorder of silica, there is an appropriate calcining temperature range. The calcining temperature is preferably from 300° C. to 1,000° C., more preferably from 500° C. to 900° C. When the calcining temperature is in this range, the additive is completely decomposed and does not adversely affect the performance of the silica carrier. In addition, the specific surface area of the silica carrier is also enhanced. The calcining treatment can be conducted under either condition of oxidizing condition and non-oxidizing condition. For example, the calcining treatment may be carried out in an air atmosphere or may be carried out in an inert gas atmosphere, such as nitrogen gas. The calcining treatment time is also not particularly limited and can be appropriately determined according to the shape and size of the molded body, the type and amount of the additive used, etc.

The silica carrier of one embodiment has, in the measurement of pore size distribution, mesopores with a pore size of 2 to 50 nm and macropores with a pore size of more than 50 nm and 1,000 nm or less. The presence of mesopores can be confirmed by a gas adsorption method (BJH method). The presence of macropores can be confirmed by mercury intrusion porosimetry. In general, the mercury intrusion porosimetry and the gas adsorption method (BJH method) are widely used for the pore size distribution measurement of a porous substance, such as silica. According to the classification of pores of IUPAC (International Union of Pure and Applied Chemistry), macropores of 50 nm or greater and part of mesopores of 2 nm to less than 50 nm can be measured by the mercury intrusion porosimetry, and mesopores and macropores of 2 nm or less can be measured by the gas adsorption method. When the silica carrier has macropores of the above-described size, the diffusion rate of a substance within a pore is more enhanced. Use of such a silica carrier in a catalyst can be expected to enhance the activity with an increase in the main reaction rate and enhance the selectivity by virtue of suppressing sequential side reactions of the target product. When the silica carrier has mesopores of the above-described size together with macropores, the supported component can be highly dispersed, and the catalytic activity can be expected to be enhanced by virtue of increasing reaction active sites.

In the silica carrier, the distribution ratio of respective pores is not particularly limited, and an appropriate pore size distribution ratio can be selected depending on the type of reaction using the silica carrier. The pore size distribution ratio can be adjusted by the mixing ratio of fumed silica, silica gel and colloidal silica at the time of production of the silica carrier, the type and amount of the additive used, the calcining temperature, the molding method, etc.

In the pore size distribution by mercury intrusion porosimetry, the pore volume of macropores (the integrated value of all macropores' volume) of the silica carrier is preferably from 0.05 to 0.50 cc/g. The pore volume of macropores of the silica carrier is more preferably from 0.07 to 0.40 cc/g, still more preferably from 0.10 to 0.30 cc/g. When the pore volume of macropores of the silica carrier is from 0.05 to 0.50 cc/g, both the diffusion rate of substance and the strength of carrier can be satisfied.

The specific surface area by the BET method (BET specific surface area) of the silica carrier is preferably from 200 to 500 $m^2/g$. The BET specific surface area of the silica carrier is more preferably from 220 to 400 $m^2/g$, still more preferably from 240 to 400 $m^2/g$. When the BET specific surface area of the silica carrier is from 200 to 500 $m^2/g$, a sufficient reaction rate can be obtained when the silica carrier is incorporated into a catalyst.

The bulk density of the silica carrier is preferably from 300 to 700 g/L. The bulk density of the silica carrier is more preferably from 400 to 650 g/L, still more preferably from 450 to 600 g/L. When the bulk density of the silica carrier is from 300 to 700 g/L, a necessary amount of active component can be supported on the silica carrier and at the same time, the strength of carrier can be maintained.

The average pore size of mesopores by the gas adsorption method (BJH method) of the silica carrier is preferably from 3 to 16 nm. The average pore size of mesopores by the gas adsorption method (BJH method) of the silica carrier is more preferably from 4 to 14 nm, still more preferably from 5 to 12 nm. When the average pore size of mesopores by the gas adsorption method (BJH method) of the silica carrier is from 3 to 16 nm, the specific surface area by the BET method is a sufficient value.

In the present description, the pore size distribution by the gas adsorption method (BJH method), the pore size distribution by mercury intrusion porosimetry, the BET specific surface area, the bulk density, and the average pore size of mesopores by the BJH method are measured by the methods described in Examples.

The heteropolyacid consists of a central element and peripheral elements to which oxygen is bonded. The central element is usually silicon or phosphorus but may be composed of any one element selected from various elements of Groups 1 to 17 of the Periodic Table of the Elements. Specifically, these may include, but are not limited to, for example, cupric ions; divalent beryllium, zinc, cobalt or nickel ions; trivalent boron, aluminum, gallium, iron, cerium, arsenic, antimony, phosphorus, bismuth, chromium or rhodium ions; tetravalent silicon, germanium, tin, titanium, zirconium, vanadium, sulfur, tellurium, manganese, nickel, platinum, thorium, hafnium, cerium ions and other rare earth ions; pentavalent phosphorus, arsenic, vanadium or antimony ions; hexavalent tellurium ions; and heptavalent iodine ions. In addition, specific examples of the peripheral element may include, but are not limited to, tungsten, molybdenum, vanadium, niobium, and tantalum.

Such a heteropolyacid is also known as "polyoxoanion", "polyoxometallates" or "metal oxide cluster". The structures of some of the wellknown anions are named after the original researchers in this field, such as the structures known as Keggin, Wells-Dawson and Anderson-Evans-Perloff structures. Details are described in "Poly-san no Kagaku (Chemistry of Polyacid)" (edited by The Chemical Society of Japan, Quaternary Chemical Review, No. 20, 1993). The heteropolyacid usually has a high molecular weight, for example, a molecular weight of 700 to 8,500 and includes not only monomeric but also dimeric complexes thereof.

The salt of heteropolyacid is not particularly limited as long as it is a metal salt or onium salt formed by substituting a part or all of hydrogen atoms of the above heteropolyacid. Specifically, examples thereof may include, but are not limited to, metal salts of lithium, sodium, potassium, cesium, magnesium, barium, copper, gold and gallium, and onium salts, such as ammonia.

The heteropolyacid has a relatively high solubility in a polar solvent, such as water or other oxygenated solvents, particularly when the heteropolyacid is a free acid or a certain salt, which solubility can be controlled by appropriately selecting the counter ion.

Examples of the heteropolyacid which can be particularly preferably used as a catalyst in the present invention may include:

silicotungstic acid $H_4[SiW_{12}O_{40}] \cdot xH_2O$,
phosphotungstic acid $H_3[PW_{12}O_{40}] \cdot xH_2O$,
phosphomolybdic acid $H_3[PMo_{12}O_{40}] \cdot xH_2O$,
silicomolybdic acid $H_4[SiMo_{12}O_{40}] \cdot xH_2O$,
silicovanadotungstic acid $H_{4+n}[SiV_nW_{12-n}O_{40}] \cdot xH_2O$,
phosphovanadotungstic acid $H_{3+n}[PV_nW_{12-n}O_{40}] \cdot xH_2O$,
phosphovanadomolybdic acid $H_{3+n}[PV_nMo_{12-n}O_{40}] \cdot xH_2O$,
silicovanadomolybdic acid $H_{4+n}[SiV_nMo_{12-n}O_{40}] \cdot xH_2O$,
silicomolybdotungstic acid $H_4[SiMo_nW_{12-n}O_{40}] \cdot xH_2O$, and
phosphomolybdotungstic acid $H_3[PMo_nW_{12-n}O_{40}] \cdot xH_2O$, wherein n is an integer of 1 to 11, and x is an integer of 1 or greater.

The heteropolyacid is preferably silicotungstic acid, phosphotungstic acid, phosphomolybdic acid, silicomolybdic acid, silicovanadotungstic acid or phosphovanadotungstic acid, more preferably silicotungstic acid, phosphotungstic acid, silicovanadotungstic acid or phosphovanadotungstic acid.

The synthesis method for such a heteropolyacid is not particularly limited, and any method may be used. For example, the heteropolyacid can be obtained by heating an acidic aqueous solution (pH: approximately from 1 to 2) containing a salt of molybdic acid or tungstic acid and a simple oxygen acid of heteroatom or a salt thereof. The heteropolyacid compound can be isolated, for example, by crystallizing and separating the compound as a metal salt from the produced aqueous heteropolyacid solution. Specific examples of the production of heteropolyacid are described on page 1413 of Shin Jikken Kagaku Koza 8, Muki Kagobutsuno Gosei (III) (New Experimental Chemistry Course 8, Synthesis of Inorganic Compounds (III)) (3rd ed., edited by The Chemical Society of Japan, published by Maruzen, Aug. 20, 1984), but the present invention is not limited thereto. The structure of the synthesized heteropolyacid can be confirmed by X-ray diffraction or UV or IR measurement, in addition to chemical analysis.

Preferable examples of the heteropolyacid salt include lithium salts, sodium salts, potassium salts, cesium salts, magnesium salts, barium salts, copper salts, gold salts, gallium salts and ammonium salts of the above-described preferable heteropolyacids.

Specific examples of the heteropolyacid salt may include lithium salt of silicotungstic acid, sodium salt of silicotungstic acid, cesium salt of silicotungstic acid, copper salt of silicotungstic acid, gold salt of silicotungstic acid, gallium salt of silicotungstic acid; lithium salt of phosphotungstic acid, sodium salt of phosphotungstic acid, cesium salt of phosphotungstic acid, copper salt of phosphotungstic acid, gold salt of phosphotungstic acid, gallium salt of phosphotungstic acid; lithium salt of phosphomolybdic acid, sodium salt of phosphomolybdic acid, cesium salt of phosphomolybdic acid, copper salt of phosphomolybdic acid, gold salt of phosphomolybdic acid, gallium salt of phosphomolybdic acid; lithium salt of silicomolybdic acid, sodium salt of silicomolybdic acid, cesium salt of silicomolybdic acid, copper salt of silicomolybdic acid, gold salt of silicomolybdic acid, gallium salt of silicomolybdic acid; lithium salt of silicovanadotungstic acid, sodium salt of silicovanadotungstic acid, cesium salt of silicovanadotungstic acid, copper salt of silicovanadotungstic acid, gold salt of silicovanadotungstic acid, gallium salt of silicovanadotungstic acid; lithium salt of phosphovanadotungstic acid, sodium salt of phosphovanadotungstic acid, cesium salt of phosphovanadotungstic acid, copper salt of phosphovanadotungstic acid, gold salt of phosphovanadotungstic acid, gallium salt of phosphovanadotungstic acid; lithium salt of phosphovanadomolybdic acid, sodium salt of phosphovanadomolybdic acid, cesium salt of phosphovanadomolybdic acid, copper salt of phosphovanadomolybdic acid, gold salt of phosphovanadomolybdic acid, gallium salt of phosphovanadomolybdic acid; lithium salt of silicovanadomolybdic acid, sodium salt of silicovanadomolybdic acid, cesium salt of silicovanadomolybdic acid, copper salt of silicovanadomolybdic acid, gold salt of silicovanadomolybdic acid, and gallium salt of silicovanadomolybdic acid.

The heteropolyacid salt is preferably lithium salt of silicotungstic acid, sodium salt of silicotungstic acid, cesium salt of silicotungstic acid, copper salt of silicotungstic acid, gold salt of silicotungstic acid, gallium salt of silicotungstic acid; lithium salt of phosphotungstic acid, sodium salt of phosphotungstic acid, cesium salt of phosphotungstic acid, copper salt of phosphotungstic acid, gold salt of phosphotungstic acid, gallium salt of phosphotungstic acid; lithium salt of phosphomolybdic acid, sodium salt of phosphomolybdic acid, cesium salt of phosphomolybdic acid, copper salt of phosphomolybdic acid, gold salt of phosphomolybdic acid, gallium salt of phosphomolybdic acid; lithium salt of silicomolybdic acid, sodium salt of silicomolybdic acid, cesium salt of silicomolybdic acid, copper salt of silicomolybdic acid, gold salt of silicomolybdic acid, gallium salt of silicomolybdic acid; lithium salt of silicovanadotungstic acid, sodium salt of silicovanadotungstic acid, cesium salt of silicovanadotungstic acid, copper salt of silicovanadotungstic acid, gold salt of silicovanadotungstic acid, gallium salt of silicovanadotungstic acid; lithium salt of phosphovanadotungstic acid, sodium salt of phosphovanadotungstic acid, cesium salt of phosphovanadotungstic acid, copper salt of phosphovanadotungstic acid, gold salt of phosphovanadotungstic acid, or gallium salt of phosphovanadotungstic acid.

The heteropolyacid salt is more preferably lithium salt of silicotungstic acid, sodium salt of silicotungstic acid, cesium salt of silicotungstic acid, copper salt of silicotungstic acid, gold salt of silicotungstic acid, gallium salt of silicotungstic acid; lithium salt of phosphotungstic acid, sodium salt of phosphotungstic acid, cesium salt of phosphotungstic acid, copper salt of phosphotungstic acid, gold salt of phosphotungstic acid, gallium salt of phosphotungstic acid; lithium salt of silicovanadotungstic acid, sodium salt of silicovanadotungstic acid, cesium salt of silicovanadotungstic acid, copper salt of silicovanadotungstic acid, gold salt of silicovanadotungstic acid, gallium salt of silicovanadotungstic acid; lithium salt of phosphovanadotungstic acid, sodium salt of phosphovanadotungstic acid, cesium salt of phosphovanadotungstic acid, copper salt of phosphovanadotungstic acid, gold salt of phosphovanadotungstic acid, or gallium salt of phosphovanadotungstic acid.

As the heteropolyacid salt, use of a lithium salt of silicotungstic acid or cesium salt of phosphotungstic acid is particularly preferable.

The above-described silica carrier is used as the carrier.

The carrier may have any shape, and the shape thereof is not particularly limited. The carrier may have, for example, a powder shape, a spherical shape, or a pellet shape and preferably has a spherical shape or a pellet shape. The particle diameter of the carrier is also not particularly limited. The particle diameter of the carrier varies depending on the form of reaction, but in the case of use in a fixed bed system, the particle diameter is preferably from 2 mm to 10 mm, more preferably from 3 mm to 7 mm.

The method for supporting the heteropolyacid or a salt thereof on a carrier is not particularly limited. In general, this can be carried out by allowing the carrier to absorb a solution or suspension obtained by dissolving or suspending the heteropolyacid or a salt thereof in a solvent, and evaporating the solvent.

The method for supporting a heteropolyacid salt on a carrier includes, but is not limited to, a method of supporting a heteropolyacid on a carrier and then supporting a raw material of a salt-forming element, a method of supporting a heteropolyacid and a raw material of a salt-forming element together on a carrier, a method of supporting a previously prepared heteropolyacid salt on a carrier, and a method of supporting a raw material of a salt-forming element on a carrier and then supporting a heteropolyacid. In all of the above methods, the heteropolyacid, the salt thereof, and the raw material of a salt-forming element can be dissolved or suspended in an appropriate solvent and supported on a carrier. The solvent may be sufficient if it can dissolve or suspend the heteropolyacid, the salt thereof, or the raw material of a salt-forming element, and water, an organic solvent or a mixture thereof may be used. Water, an alcohol, or a mixture thereof is preferably used.

Supporting the heteropolyacid or a salt thereof on a carrier can be adjusted, specifically, for example, by dissolving the heteropolyacid or salt thereof in distilled water, etc., of an amount corresponding to the liquid volume of water to be absorbed by the carrier, and impregnating the carrier with the solution. In another embodiment, the amount of a heteropolyacid or a salt thereof supported on a carrier can also be adjusted by impregnating the carrier while moderately moving it in an excess amount of solution of the heteropolyacid or salt thereof and then carrying out filtration to remove excess heteropolyacid or salt thereof. The volume of the solution or suspension varies depending on the carrier, supporting method, etc., used. The carrier impregnated with the heteropolyacid or salt thereof is placed in a heating oven for several hours to evaporate the solvent, and a solid acid catalyst supported on a carrier can thereby obtained. The drying method is not particularly limited, and various methods, such as a still standing or belt conveyor system, can be used.

As for the amount of a heteropolyacid or a salt thereof supported on a carrier, the total mass of the heteropolyacid or salt thereof is preferably from 10 to 150 parts by mass, more preferably from 30 to 100 parts by mass, per 100 parts by mass of the carrier.

<Production of Aliphatic Carboxylic Acid>

In the present invention, the aliphatic carboxylic acid ester can be obtained by reacting an aliphatic carboxylic acid having from 1 to 5 carbon atoms and an olefin having from 2 to 4 carbon atoms in a gas phase by using a heteropolyacid or a salt thereof as a solid acid catalyst. From the viewpoint of removing heat of reaction, the aliphatic carboxylic acid and olefin are preferably diluted with an inert gas, such as nitrogen gas. Specifically, a gas containing, as raw materials, an aliphatic carboxylic acid having from 1 to 5 carbon atoms and an olefin having from 2 to 4 carbon atoms is flowed through a vessel filled with a solid acid catalyst to come into contact with the solid acid catalyst, and these can thereby be reacted. From the viewpoint of maintaining catalytic activity, it is preferable to add a small amount of water to the raw material containing gas, and in an embodiment, the reaction is carried out in the presence of water vapor. However, if a too large an amount of water is added, the production of byproducts, such as alcohol and ether, may be increased. The amount of water added is preferably from 0.5 mol % to 15 mol %, more preferably from 2 mol % to 8 mol %, in terms of molar ratio of water to the total of an aliphatic carboxylic acid having from 1 to 5 carbon atoms, an olefin having from 2 to 4 carbon atoms, and water.

The aliphatic carboxylic acid having from 1 to 5 carbon atoms may include formic acid, acetic acid, propionic acid, valeric acid, methacrylic acid, and crotonic acid. Acetic acid is preferred in view of, for example, ease of availability of raw materials and industrial usefulness of the produced carboxylic acid ester.

The olefin having from 2 to 4 carbon atoms may include ethylene, propylene, 1-butene, 2-butene, and isobutene. Ethylene and propylene are preferred in view of, for example, ease of availability of raw materials and industrial usefulness of the produced carboxylic acid ester.

The usage ratio between the olefin having from 2 to 4 carbon atoms and the aliphatic carboxylic acid having from 1 to 5 carbon atoms as raw materials is not particularly limited but is, in terms of the molar ratio between olefin and aliphatic carboxylic acid, preferably olefin:aliphatic carboxylic acid=from 1:1 to 40:1, more preferably from 3:1 to 20:1, still more preferably from 5:1 to 15:1.

The preferable reaction conditions, such as temperature and pressure, in the production method of the present invention vary according to the types of the aliphatic carboxylic acid and olefin used as raw materials. The combination of reaction conditions, such as temperature and pressure, is preferably in a range where the raw material can keep the gas state and the reaction sufficiently proceeds. In general, the reaction temperature is preferably from 50° C. to 300° C., more preferably from 140° C. to 250° C., and the reaction pressure is preferably from 0 PaG to 3 MPaG (gauge pressure), more preferably from 0.1 MPaG to 2 MPaG (gauge pressure). In an embodiment, the reaction temperature is from 50 to 300° C., and the reaction pressure is from 0.1 to 2.0 MPaG.

The SV (gas hourly space velocity) of the raw material containing gas is not particularly limited, but if it is too large, the raw materials pass through in a stage of the reaction having not sufficiently proceeded, and on the other hand, if it is too small, there may be a problem of, for example, a reduction in productivity. SV (the volume of raw material passing through in 1 hour per L of the catalyst (L/L·h=h$^{-1}$)) is preferably from 500 h$^{-1}$ to 20,000 h$^{-1}$, more preferably from 1,000 h$^{-1}$ to 10,000 h$^{-1}$.

EXAMPLES

The present invention is further described below by referring to Examples and Comparative Examples, but the present invention is not limited to the following Examples.

1. Production of Silica Carrier

Fumed silica, silica gel, colloidal silica, and, if desired, water and/or additives were put in a kneader and kneaded to prepare a kneaded product. Subsequently, the kneaded product was charged into an extrusion molding machine attached with a die having provided at the tip thereof a circular hole with a desired size. Furthermore, an intermediate extruded from the extrusion molding machine was cut by a cutter into a desired size to obtain a columnar molded body before calcining. The molded body before calcining was treated with Marumerizer, then preliminarily dried, and furthermore subjected to a calcining treatment at a temperature of 700° C. to 900° C. in an air atmosphere to obtain a silica carrier. Detailed conditions are described in each production example.

2. Measurement of Bulk Density of Silica Carrier

The silica carrier was charged in several batches into a glass-made measuring cylinder which was tared and at the same time, the measuring cylinder containing the carrier or catalyst (a catalyst metal, etc., was supported on the carrier) was tapped at every charging. The carrier was charged until reaching just the metric volume of the measuring cylinder. Subsequently, the weight of the measuring cylinder in the state of the carrier contained therein was measured, and the bulk density of the carrier was determined by the tare and volume of the measuring cylinder.

3. Measurement of BET Specific Surface Area of Silica Carrier

The BET specific surface area by nitrogen gas adsorption of the silica carrier or catalyst was measured using a gas adsorption system (ASAP 2020) manufactured by Shimadzu Corporation. In addition, the pore size distribution of the silica carrier according to the BJH method was measured, and the average pore size of mesopores was measured.

4. Measurement of Pore Size Distribution by Mercury Intrusion Porosimetry of Silica Carrier The pore size distribution of the silica carrier according to mercury intrusion porosimetry was measured using Autopore IV9500 manufactured by Shimadzu Corporation. Furthermore, in the pore size distribution, the peak pore volume (cc/g) derived from macropores of 30 to 300 nm was measured.

5. Raw Material Silicas

The raw material silicas used are shown in Table 1.

TABLE 1

|  | No. | Specific Surface Area ($m^2/g$) | Average Pore Size (nm) | Average Particle Diameter (μm) | Purity (%) |
|---|---|---|---|---|---|
| Fumed silica | F-1 | 380 | no pore | 0.007 | 99.9 |
|  | F-2 | 200 | no pore | 0.012 | 99.9 |
| Silica gel | S-1 | 500 | 6 | 5 | 99.9 |
|  | S-2 | 360 | 8 | 5 | 99.9 |
|  | S-3 | 300 | 10 | 5 | 99.9 |
|  | S-4 | 850 | 5 | 5 | 99.9 |
| Colloidal silica*[)] | C-1 | — | — | 0.012 | — |

*[)]Solid content: 20 mass %

Production Example 1

Figure 2:
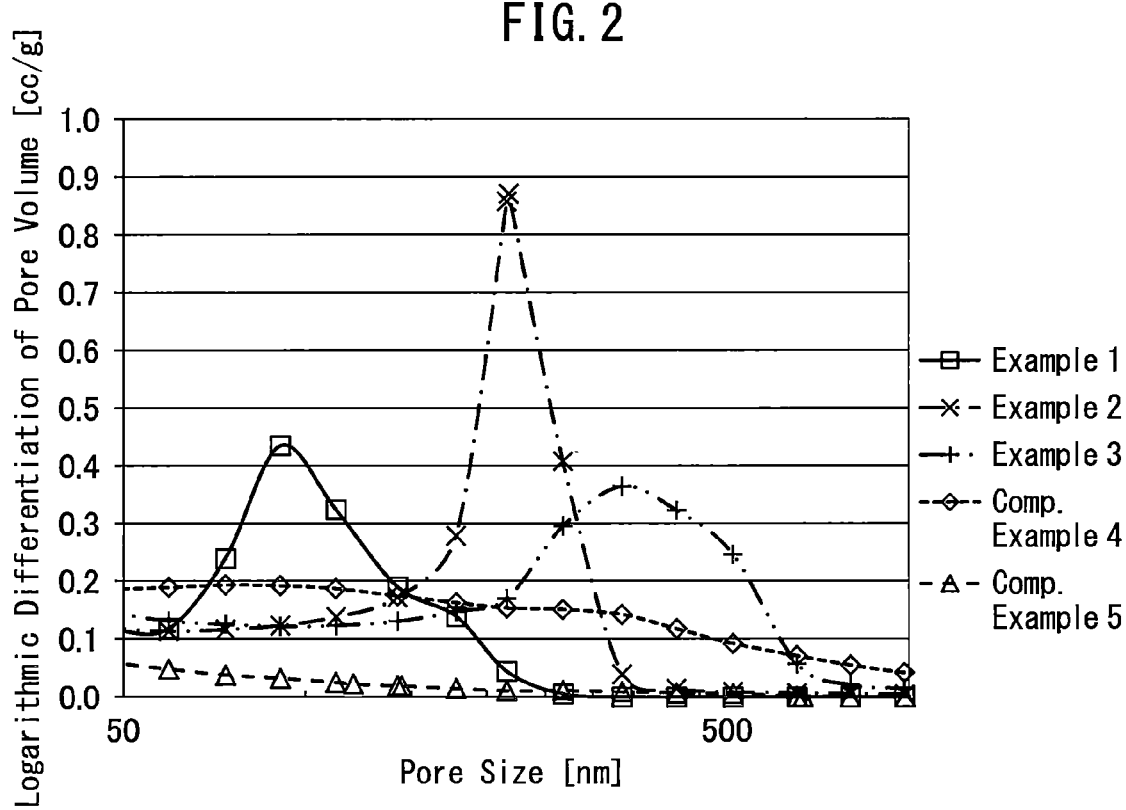
FIG. 2 A graph illustrating the pore size distribution by mercury intrusion porosimetry of the silica carriers used in Examples 1 to 3 and Comparative Examples 4 and 5.

25 Parts by mass of Fumed Silica F-1, 75 parts by mass of Silica Gel S-1, and 45 parts by mass (9 parts by mass as solid content) of Colloidal Silica C-1 were kneaded in a kneader, and while observing the condition of the kneaded product, appropriate amounts of water and additives (methyl cellulose: SM-4000 produced by Shin-Etsu Chemical Co., Ltd., 10 parts by mass; resin-based binder: Serander (trademark) YB-132A produced by Yuken Industry Co., Ltd., 5 parts by mass) were added. The mixture was further kneaded to obtain a kneaded product. The kneaded product was then charged into an extrusion molding machine attached with a die having provided thereon a circular hole of 6 mmp and by extruding the kneaded product, extrusion molding was carried out while cutting the extruded intermediate by a cutter such that the length thereof is the same length as the diameter of the circular hole. The resulting molded body before calcining was formed into a spherical shape by Marumerizer (trademark), then dried at 70° C. for 24 hours or longer, furthermore calcined at about 820° C. in an air atmosphere, and cooled to obtain Silica Carrier A. The measurement results of BET specific surface area, average pore size by the BJH method, bulk density, etc., of the obtained Silica Carrier A are shown in Table 2. In addition, FIG. 1 illustrates the pore size distribution by the BJH method of Silica Carrier A, and FIG. 2 illustrates the measurement results of the pore size distribution by mercury intrusion porosimetry.

Production Examples 2 to 11

Silica Carriers B to K were obtained in the same manner as in Production Example 1, except that the types and amounts of fumed silica, silica gel and colloidal silica and the calcining temperature were changed as shown in Table 2. However, in Production Examples 4 to 11, a die having provided thereon a circular hole of 3 mmp was used. The measurement results of BET specific surface area, average pore size by the BJH method, bulk density, etc., of each of the obtained silica carriers are shown in Table 2. In addition, FIG. 2 illustrates the measurement results of the pore size distribution by mercury intrusion porosimetry of Silica Carriers B and C.

Comparative Production Example 1

Production of the silica carrier of Comparative Production Example 1 was tried in the same manner as in Example 1, except for not using colloidal silica, but a molded body usable as a carrier was not obtained.

Comparative Production Example 2

Production of the silica carrier of Comparative Production Example 2 was tried in the same manner as in Example 1, except for not using fumed silica, but a molded body usable as a carrier was not obtained.

Comparative Production Example 3

Production of the silica carrier of Comparative Production Example 3 was tried in the same manner as in Example 1, except for not using silica gel, but a molded body usable as a carrier was not obtained.

Comparative Carrier Example 4

The measurement results of BET specific surface area, average pore size by the BJH method, bulk density, etc., of commercially available silica carrier KA-160 (Silica Carrier P) produced by Clamant Catalyst Corporation, which is a natural product-derived silica gel, are shown in Table 3. In addition, FIG. 1 illustrates the pore size distribution by the BJH method of Silica Carrier P, and FIG. 2 illustrates the measurement results of the pore size distribution by mercury intrusion porosimetry.

Comparative Carrier Example 5

The measurement results of BET specific surface area, average pore size by the BJH method, bulk density, etc., of silica carrier CARiACT Q-15 (Silica Carrier Q) produced by Fuji Silysia Chemical Ltd., which is a commercially available silica gel, are shown in Table 3. In addition, FIG. 1 illustrates the pore size distribution by the BJH method of Silica Carrier Q, and FIG. 2 illustrates the measurement results of the pore size distribution by mercury intrusion porosimetry.

Comparative Carrier Example 6

The measurement results of BET specific surface area, average pore size by the BJH method, bulk density, etc., of silica carrier CARiACT Q-30 (Silica Carrier R) produced by Fuji Silysia Chemical Ltd., which is a commercially available silica gel, are shown in Table 3. In addition, FIG. 1 illustrates the measurement results of the pore size distribution by the BJH method of Silica Carrier R.

Comparative Carrier Example 7

The measurement results of BET specific surface area, average pore size by the BJH method, bulk density, etc., of silica carrier CARiACT Q-10 (Silica Carrier S) produced by Fuji Silysia Chemical Ltd., which is a commercially available silica gel, are shown in Table 3.

Comparative Carrier Example 8

The measurement results of BET specific surface area, average pore size by the BJH method, bulk density, etc., of silica carrier CARiACT Q-6 (Silica Carrier T) produced by Fuji Silysia Chemical Ltd., which is a commercially available silica gel, are shown in Table 3.

TABLE 2

| Silica Carrier | Particle Diameter (mm) | Fumed Silica Type | Fumed Silica Blending Amount parts by mass | Fumed Silica Blending Amount mass % | Silica Gel Type | Silica Gel Blending Amount parts by mass | Silica Gel Blending Amount mass % | Colloidal Silica Type | Colloidal Silica Blending Amount (solid content) parts by mass | Colloidal Silica Blending Amount (solid content) mass % | Calcining Temperature (°C) | BET Specific Surface Area (m²/g) | Average Pore Size by BJH Method (nm) | Bulk Density (g/L) | Presence or Absence of Mesopores | Presence of Absence of Macropores | Pore Volume of Macropores (cc/g) |
|---|---|---|---|---|---|---|---|---|---|---|---|---|---|---|---|---|---|
| A | 6 | F-1 | 25 | 22.9 | S-1 | 75 | 68.8 | C-1 | 9 | 8.3 | 820 | 313 | 6.6 | 548 | present | present | 0.15 |
| B | 6 | F-1 | 25 | 22.9 | S-2 | 75 | 68.8 | C-1 | 9 | 8.3 | 820 | 286 | 9.4 | 438 | present | present | 0.22 |
| C | 6 | F-1 | 25 | 22.9 | S-3 | 75 | 68.8 | C-1 | 9 | 8.3 | 820 | 225 | 14.5 | 386 | present | present | 0.22 |
| D | 3 | F-1 | 25 | 22.9 | S-2 | 75 | 68.8 | C-1 | 9 | 8.3 | 820 | 287 | 9.4 | 439 | present | present | 0.25 |
| E | 3 | F-1 | 25 | 22.9 | S-1 | 75 | 68.8 | C-1 | 9 | 8.3 | 820 | 293 | 6.6 | 567 | present | present | 0.16 |
| F | 3 | F-1 | 10 | 9.2 | S-1 | 90 | 82.6 | C-1 | 9 | 8.3 | 820 | 297 | 5.5 | 619 | present | present | 0.16 |
| G | 3 | F-1 | 40 | 36.7 | S-1 | 60 | 55.0 | C-1 | 9 | 8.3 | 820 | 294 | 7.4 | 551 | present | present | 0.15 |
| H | 3 | F-2 | 25 | 22.9 | S-1 | 75 | 68.8 | C-1 | 9 | 8.3 | 820 | 273 | 6.4 | 593 | present | present | 0.11 |
| I | 3 | F-1 | 25 | 22.9 | S-1 | 75 | 68.8 | C-1 | 9 | 8.3 | 750 | 356 | 6.5 | 507 | present | present | 0.19 |
| J | 3 | F-1 | 25 | 22.9 | S-1 | 75 | 68.8 | C-1 | 9 | 8.3 | 700 | 381 | 6.5 | 481 | present | present | 0.20 |
| K | 3 | F-1 | 25 | 22.9 | S-4 | 75 | 68.8 | C-1 | 9 | 8.3 | 820 | 284 | 5.4 | 686 | present | present | 0.15 |
| L | 6 | F-1 | 25 | 25.0 | S-1 | 75 | 75.0 | — | 0 | 0.0 | 820 | could not be molded and was unusable as a carrier ||||||
| M | 6 | — | 0 | 0.0 | S-1 | 75 | 89.3 | C-1 | 9 | 10.7 | 820 | | | | | | |
| N | 6 | F-1 | 25 | 73.5 | — | 0 | 0.0 | C-1 | 9 | 26.5 | 820 | | | | | | |

TABLE 3

| No. | Silica Carrier | Product Name | Supplier | BET Specific Surface Area (m²/g) | Average Pore Size by BJH Method (nm) | Bulk Density (g/L) | Presence or Absence of Mesopores | Presence or Absence of Macropores | Pore Volume of Macropores (cc/g) |
|---|---|---|---|---|---|---|---|---|---|
| Comparative Carrier Example 4 | P | KA-160 | Clariant Catalyst Corporation | 151 | 10.8 | 579 | present | absent | (0.19) |
| Comparative Carrier Example 5 | Q | CARiACT Q-15 | Fuji Silysia Chemical Ltd. | 183 | 22.4 | 430 | present | absent | 0.02 |
| Comparative Carrier Example 6 | R | CARiACT Q-30 | Fuji Silysia Chemical Ltd. | 105 | 33.6 | 435 | absent | absent | 0.03 |
| Comparative Carrier Example 7 | S | CARiACT Q-10 | Fuji Silysia Chemical Ltd. | 305 | 11.5 | 423 | present | absent | 0.02 |

TABLE 3-continued

| No. | Silica Carrier | Product Name | Supplier | BET Specific Surface Area (m²/g) | Average Pore Size by BJH Method (nm) | Bulk Density (g/L) | Presence or Absence of Mesopores | Presence or Absence of Macropores | Pore Volume of Macropores (cc/g) |
|---|---|---|---|---|---|---|---|---|---|
| Comparative Carrier Example 8 | T | CARiACT Q-6 | Fuji Silysia Chemical Ltd. | 379 | 5.2 | 623 | present | absent | 0.01 |

As apparent from FIGS. 1 and 2, in Silica Carrier A of Production Example 1, mesopores having a peak around 4.5 nm and macropores having a peak around 90 nm are present, and the pore volume of macropores is 0.15 cc/g. On the other hand, in Silica Carriers P and Q of Comparative Carrier Examples 4 and 5, a peak corresponding to macropores is not observed from FIG. 2.

The values calculated by integrating pore volumes of macropores in the range of more than 50 nm and 1,000 nm or less from the pore size distribution by mercury intrusion porosimetry are shown in Tables 2 and 3. In all of Silica Carriers A to K of production examples, the pore volume of macropores is 0.10 cc/g or greater, but in Silica Carriers Q, S and T of Comparative Carrier Examples 5, 7 and 8, the pore volume of macropores is only less than 0.02 cc/g, and macropores are not present. Furthermore, Silica Carrier P of Comparative Carrier Example 4 is calculated to have a pore volume of macropores of 0.19 cc/g, but since a clear peak of macropores is not observed in FIG. 2, substantially no macropores are present.

<Evaluation of Catalyst Performance>

Catalysts where a heteropolyacid was supported on Silica Carriers A to C and E to H of Production Examples 1 to 3 and 5 to 8 and Silica Carriers P, Q, S and T of Comparative Carrier Examples 4, 5, 7 and 8 were prepared according to the following procedures and evaluated for the catalyst performance by using the catalyst in a reaction of producing ethyl acetate from ethylene and acetic acid.

(Preparation of Catalyst A)

40.7 g of commercially available Keggin-type silicotungstic acid $H_4SiW_{12}O_{40} \cdot 26H_2O$ (produced by Nippon Inorganic Colour & Chemical Co., Ltd.) was dissolved in 34.1 mL of distilled water. The obtained solution was then added to 100 mL (54.8 g) of Silica Carrier A and thoroughly stirred to impregnate the carrier. The carrier impregnated with the solution was transferred to a porcelain dish, air dried for 1 hours and then dried for 5 hours by a dryer adjusted to 130° C. to obtain Catalyst A.

(Preparation of Catalysts B, C and E to H and Comparative Catalysts P, Q, S and T)

Each catalyst was obtained in the same manner as in the preparation of Catalyst A, except that any of Silica Carriers B, C and E to H and Silica Carriers P, Q, S and T was used in place of Silica Carrier A.

(Catalyst Specific Surface Area)

The catalyst specific surface area of each of Catalysts A to C and E to H and Comparative Catalysts P, Q, S and T was measured as a BET specific surface area based on nitrogen gas adsorption by using a gas adsorption system (ASAP 2020) manufactured by Shimadzu Corporation.

Examples 1 to 7 and Comparative Examples 1 to 3: Production of Ethyl Acetate

A columnar SUS316L pressure-resistant vessel having a radius of 25 mm was filled with 40 mL of each of the catalysts obtained above and after the pressure was elevated to 0.75 MPaG, the temperature was raised to 155° C. A pretreatment was carried out for 30 minutes under the conditions of nitrogen gas/acetic acid (gas)/water vapor=85.5 mol %/10.0 mol %/4.5 mol %, and SV (the volume of raw material passing through in 1 hour per L of the catalyst (L/L·h=h$^{-1}$))=1,500 h$^{-1}$ and thereafter, the reaction was carried out for 5 hours under the conditions of ethylene (gas)/nitrogen gas/acetic acid (gas)/water vapor=78.5 mol %/7.0 mol %/10.0 mol %/4.5 mol % and SV=1,500 h$^{-1}$. The reaction was carried out by adjusting the reaction temperature such that out of portions formed by dividing the catalyst layer into tenths, the portion having a highest reaction temperature is at 165.0° C. The gas passed during the time period between 3 hours and 5 hours after the start of reaction was recovered in its entire amount by collecting it under ice-water cooling for a predetermined time (hereinafter, this is referred to as "condensate") and analyzed. In addition, with respect to the uncondensed gas remaining without being condensed (hereinafter, this is referred to as "uncondensed gas"), the gas flow rate was measured for the same time as that of the condensate, and a 100 mL portion thereof was taken out and analyzed. The reaction results obtained are shown in Table 4.

(Analysis Method of Condensate)

The analysis was carried out using the internal standard method under the following conditions, where the analysis solution was prepared by adding 1 mL of 1,4-dioxane as the internal standard to 10 mL of the reaction solution and a 0.2 μL portion thereof was injected.

Gas chromatography: GC-14A manufactured by Shimadzu Corporation

Column: capillary column TC-WAX (length: 30 m, inner diameter: 0.25 mm, film thickness: 0.5 μm)

Carrier gas: nitrogen (split ratio: 36, column flow rate: 1.2 mL/min)

Temperature conditions: The detector and vaporization chamber were set at a temperature of 200° C., and the column temperature was kept at 40° C. for 7 minutes from the start of analysis, then raised to 200° C. at a temperature rise rate of 10° C./min, and kept at 200° C. for 5 minutes.

Detector: FID (H$_2$ pressure: 49 kPa, air pressure: 98 kPa)

(Analysis Method of Uncondensed Gas)

The analysis was carried out using the absolute calibration curve method under the following conditions, where 100 mL of the uncondensed gas was sampled and the whole amount thereof was flowed to a 1-mL gas sampler attached to the gas chromatograph.

1. Diethyl Ether, Ethyl Acetate, and Ethanol

Gas chromatograph: 7890A manufactured by Agilent Technologies

Column: Agilent J&W GC column DB-624

Carrier gas: He (flow rate: 1.7 mL/min)

Temperature conditions: The detector and vaporization chamber were set at a temperature of 230° C., and the column temperature was kept at 40° C. for 3 minutes from the start of analysis and then raised to 200° C. at a rate of 20° C./min.

Detector: FID ($H_2$: 40 mL/min, air pressure: 400 mL/min)

2. Ethylene

Gas chromatograph: 7890A manufactured by Agilent Technologies

Column: SHIMADZU GC GasPro (30 m), Agilent J&W GC column HP-1

Carrier gas: He (flow rate: 2.7 mL/min)

Temperature conditions: The detector and vaporization chamber were set at a temperature of 230° C., and the column temperature was kept at 40° C. for 3 minutes from the start of analysis and then raised to 200° C. at a rate of 20° C./min.

Detector: FID ($H_2$: 40 mL/min, air pressure: 400 mL/min)

3. Nitrogen

Gas chromatograph: 7890A manufactured by Agilent Technologies

Column: HayesepQ G3591-80004

Carrier gas: He (flow rate: 60 psi)

Temperature conditions: The detector and vaporization chamber were set at a temperature of 230° C., and the column temperature was kept at 40° C. for 3 minutes from the start of analysis and then raised to 200° C. at a rate of 20° C./min.

Detector: TCD (He: 45 mL/min, air pressure: 2 mL/min)

TABLE 4

| No. | Example | | | | | | | Comparative Example | | | |
|---|---|---|---|---|---|---|---|---|---|---|---|
| | 1 | 2 | 3 | 5 | 6 | 7 | 8 | 4 | 5 | 7 | 8 |
| Catalyst | A | B | C | E | F | G | H | P | Q | S | T |
| Silica carrier | A | B | C | E | F | G | H | P | Q | S | T |
| EtOAc[2] STY[1] (g/h · L) | 347.2 | 318.2 | 260.8 | 337.7 | 340.5 | 345.1 | 347.2 | 213.8 | 237.3 | 290.7 | 316.8 |
| DEE[3] STY[1] (g/h · L) | 17.3 | 12.1 | 6.3 | 10.7 | 11.4 | 11.2 | 12.1 | 3.3 | 2.3 | 6.7 | 9.5 |
| EtOH[4] STY[1] (g/h · L) | 8.9 | 7.9 | 6.2 | 8.5 | 8.6 | 8.7 | 8.8 | 4.1 | 4.6 | 5.8 | 7.6 |
| EtOAc Selectivity (%) | 85.3 | 87.5 | 91.0 | 88.7 | 88.3 | 88.5 | 88.0 | 92.5 | 94.1 | 91.4 | 89.1 |
| DEE Selectivity (%) | 10.1 | 7.9 | 4.9 | 6.7 | 7.0 | 6.8 | 7.3 | 3.4 | 2.1 | 4.3 | 6.3 |
| EtOH Selectivity (%) | 4.2 | 4.1 | 3.8 | 4.2 | 4.2 | 4.2 | 4.2 | 3.4 | 3.5 | 4.0 | 4.1 |
| Catalyst specific surface area ($m^2$/mL) | 148.1 | 120.9 | 98.3 | 143.3 | 159.9 | 138.7 | 147.3 | 79.4 | 92.0 | 130.4 | 213.3 |

[1]Space-time yield, [2]ethyl acetate, [3]diethyl ether, and [4]ethanol.

Figure 3:
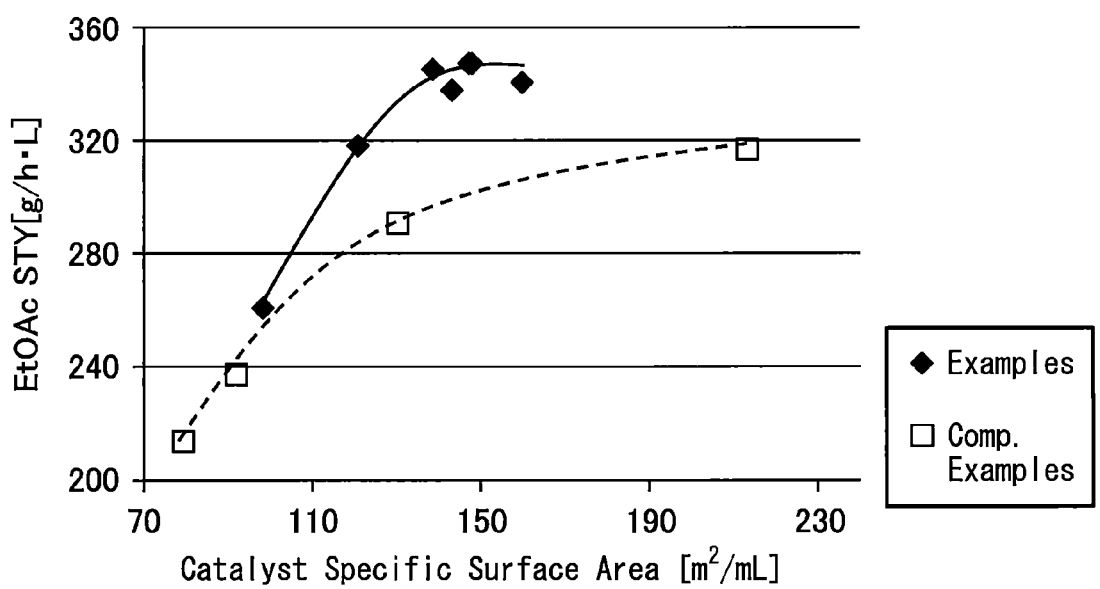
FIG. 3 A graph illustrating the relationship between the specific surface area and the reaction activity (STY) of Catalysts B, C and E to H and Comparative Catalysts P, Q, S and T.

It is known that there is generally correlation between the specific surface area and the activity of the catalyst. FIG. 3 graphically illustrates the relationship between the specific surface area and the reaction activity (STY of ethyl acetate) of Catalysts B, C and E to H and Comparative Catalysts P, Q, S and T. As seen from FIG. 3, the characteristic pore size distribution of the catalyst supported on the silica carrier of the Examples reveals that the catalyst exhibits higher activity with the same specific surface area, compared with the catalyst using a commercially available silica carrier (Silica Carriers P, Q, S and T).

In addition, it is seen that in Examples 1 and 2 and Examples 4 to 7 where the silica carrier has a large pore volume of macropores and a large BET specific surface area at the same time, the catalyst exhibits higher activity, compared with the catalyst using a commercially available silica carrier (Silica Carriers P, Q, S and T).

INDUSTRIAL APPLICABILITY

The present invention enhances in the production efficiency of an aliphatic carboxylic acid ester, such as ethyl acetate, and is useful in industry.

The invention claimed is:

1. A method for producing an aliphatic carboxylic acid ester comprising the steps of:
   1) kneading fumed silica obtained by a combustion method, silica gel obtained by a gel method, and colloidal silica obtained by a sol-gel method or a water glass method, molding the resulting kneaded product, and calcining the resulting molded body to obtain a silica carrier;
   2) supporting a heteropolyacid or a salt thereof on the silica carrier to obtain a solid acid catalyst; and
   3) reacting an aliphatic carboxylic acid having from 1 to 5 carbon atoms and an olefin having from 2 to 4 carbon atoms in a gas phase by use of the solid acid catalyst.

2. The method for producing an aliphatic carboxylic acid ester according to claim 1, wherein, in step 1), the blending amount of fumed silica is from 4.0 to 52.6 mass %, the blending amount of silica gel is from 33.3 to 90.0 mass %, and the blending amount of the solid content of colloidal silica is from 3.4 to 40.0 mass %, provided that the total amount of the fumed silica, the silica gel, and the solid content of the colloidal silica is 100 mass %.

3. The method for producing an aliphatic carboxylic acid ester according to claim 1, wherein the calcining temperature is from 300 to 1,000° C. in step 1).

4. The method for producing an aliphatic carboxylic acid ester according to claim 1, wherein the silica carrier obtained in step 1) has, in the measurement of pore size distribution, mesopores with a pore size of 2 to 50 nm and macropores with a pore size of more than 50 nm and 1,000 nm or less.

5. The method for producing an aliphatic carboxylic acid ester according to claim 1, wherein in the pore size distribution by mercury intrusion porosimetry, the pore volume of macropores of the silica carrier is from 0.05 to 0.50 cc/g.

6. The method for producing an aliphatic carboxylic acid ester according to claim 1, wherein the BET specific surface area of the silica carrier is from 200 to 500 $m^2$/g.

7. The method for producing an aliphatic carboxylic acid ester according to claim 1, wherein the bulk density of the silica carrier is from 300 to 700 g/L.

8. The method for producing an aliphatic carboxylic acid ester according to claim 1, wherein the average pore size of mesopores by the BJH method of the silica carrier is from 3 to 16 nm.

9. The method for producing an aliphatic carboxylic acid ester according to claim 1, wherein the particle diameter of the silica carrier is from 2 to 8 mm.

\* \* \* \* \*